US007958485B2

(12) United States Patent
Steiner et al.

(10) Patent No.: US 7,958,485 B2
(45) Date of Patent: Jun. 7, 2011

(54) METHODS AND SYSTEMS FOR MANAGING CONTENT DEPENDENCY DEPLOYMENT

(75) Inventors: David John Steiner, Kaysville, UT (US); Timothy Paul Hanna, Cedar Hills, UT (US)

(73) Assignees: General Electric Company, Schenectady, NY (US); IHC Health Services, Inc., Salt Lake City, UT (US)

( * ) Notice: Subject to any disclaimer, the term of this patent is extended or adjusted under 35 U.S.C. 154(b) by 867 days.

(21) Appl. No.: 11/943,980

(22) Filed: Nov. 21, 2007

(65) Prior Publication Data

US 2009/0132587 A1 May 21, 2009

(51) Int. Cl.
*G06F 9/44* (2006.01)

(52) U.S. Cl. ........ 717/103; 717/102; 717/106; 717/176; 717/177; 709/201; 709/203

(58) Field of Classification Search .................. None
See application file for complete search history.

(56) References Cited

U.S. PATENT DOCUMENTS

| 5,471,382 | A | 11/1995 | Tallman et al. |
| 5,764,923 | A | 6/1998 | Tallman et al. |
| 6,206,829 | B1 | 3/2001 | Iliff |
| 6,421,650 | B1 | 7/2002 | Goetz et al. |
| 6,482,156 | B2 | 11/2002 | Iliff |
| 6,542,902 | B2 | 4/2003 | Dulong et al. |
| 6,606,744 | B1 * | 8/2003 | Mikurak ........................ 717/174 |
| 6,694,334 | B2 | 2/2004 | DuLong et al. |
| 6,785,704 | B1 * | 8/2004 | McCanne ...................... 718/105 |
| 6,826,578 | B2 | 11/2004 | Brackett et al. |
| 7,124,101 | B1 * | 10/2006 | Mikurak ........................ 705/35 |
| 7,165,041 | B1 * | 1/2007 | Guheen et al. .................. 705/10 |
| 7,275,220 | B2 | 9/2007 | Brummel |
| 7,703,073 | B2 * | 4/2010 | Illowsky et al. ............... 717/121 |
| 2002/0010798 | A1 * | 1/2002 | Ben-Shaul et al. ........... 709/247 |
| 2003/0018612 | A1 * | 1/2003 | Melbin ............................. 707/1 |
| 2003/0028796 | A1 * | 2/2003 | Roberts et al. ................ 713/193 |
| 2003/0120593 | A1 * | 6/2003 | Bansal et al. .................... 705/39 |
| 2005/0010653 | A1 * | 1/2005 | McCanne ...................... 709/219 |
| 2005/0262477 | A1 * | 11/2005 | Kovachka-Dimitrova et al. ............................. 717/118 |
| 2005/0273787 | A1 * | 12/2005 | Kovachka-Dimitrova et al. ............................. 719/310 |
| 2008/0028395 | A1 * | 1/2008 | Motta et al. .................... 717/177 |
| 2008/0060003 | A1 * | 3/2008 | Nocifera et al. ................. 725/35 |
| 2008/0162609 | A1 * | 7/2008 | Bigian et al. .................. 707/205 |
| 2009/0100147 | A1 * | 4/2009 | Igarashi ........................ 709/218 |
| 2009/0254572 | A1 * | 10/2009 | Redlich et al. .................. 707/10 |
| 2009/0307307 | A1 * | 12/2009 | Igarashi ........................ 709/203 |
| 2010/0161656 | A1 * | 6/2010 | Roberts et al. ................ 707/769 |

OTHER PUBLICATIONS

Title: A content placement and management system for distributed Web-server systems, author: Yang et al, dated: Aug. 6, 2002, source: IEEE.*
Title: A Management System for Distributed Knowledge and Content Objects, author: Behrendt, W et al, source: IEEE, dated: Dec. 26, 2006.*

* cited by examiner

*Primary Examiner* — Chameli C Das
(74) *Attorney, Agent, or Firm* — Armstrong Teasdale LLP

(57) ABSTRACT

A method for managing electronic content includes obtaining the content and associating top level contents of the obtained content with a deployment set. The top level content includes content that is specified by a user for deployment. The method also includes determining all dependencies of dependent content for each of the associated top level contents in the deployment set, incorporating the determined dependencies into discharge instructions for the deployment set, and generating a content deployment block including the associated top level contents, the dependent content, and the discharge instructions for the deployment set. The discharge instructions include dependency ordered deployment commands.

20 Claims, 4 Drawing Sheets

METHODS AND SYSTEMS FOR MANAGING CONTENT DEPENDENCY DEPLOYMENT

BACKGROUND OF THE INVENTION

This invention relates generally to content management systems and more particularly, to methods and systems for managing content dependency deployment in content management systems.

At least some known content management systems (CMS) contain terminology style clinical content and/or full knowledge clinical content. These types of clinical content respectively range from structured or unstructured textual content to more complex content such as, but not limited to, images, multimedia files, music, audio, driver/software downloads, code, markup eXtensible Markup Language XML structures, PDF files, and/or formatted documents originating from similar or disparate databases and/or repositories. At least some known CMS are utilized in knowledge-based industries such as, but not limited to, the healthcare industry to share the clinical content with various individuals.

Generally, electronic clinical content is transferred internally or externally between various systems such that clinical information can be shared between various healthcare individuals. At least some known electronic clinical content include interdependent rules, applications, protocols, documents, links to web content, care plans, templates, controlled terminology, and/or other relationships. Known CMS generally lack sufficient information and/or metadata capable of handling both terminology content and knowledge content within a single source system.

Because some known CMS have difficulty handling both terminology content and knowledge content, the associated interdependencies are not properly managed. If the interdependencies are not deployed to a target system in the right place, in the right order, and at the right time, some known content deployment methods and systems generally experience problems that affect the efficiencies and effectiveness in deploying clinical content, which include multiple interdependencies, between the various systems. As such, access to clinical content is constrained by problems of interoperation such as, but not limited to, broken links, broken images, and/or lengthy run-time deployment.

BRIEF DESCRIPTION OF THE INVENTION

A method for managing electronic content is provided. The method includes obtaining the content and associating top level contents of the obtained content with a deployment set. The top level content includes content that is specified by a user for deployment. The method also includes determining all dependencies of dependent content for each of the associated top level contents in the deployment set, incorporating the determined dependencies into discharge instructions for the deployment set, and generating a content deployment block including the associated top level contents, the dependent content, and the discharge instructions for the deployment set. The discharge instructions include dependency ordered deployment commands.

A system for managing electronic content is provided. The system includes a source system configured to obtain the content, associate top level contents of the obtained content with a deployment set, determine all dependencies of dependent content for each of the associated top level contents in said deployment set, and incorporate the determined dependencies into discharge instructions for the deployment set. The top level content includes content that is specified by a user for deployment. The system also includes a content deployment block generated by the source system. The content deployment block includes the associated top level contents, the dependent content, and the discharge instructions for the deployment set. The discharge instructions include dependency ordered deployment commands.

A system for managing electronic content of a deployment set is provided. The system includes a source system and a content deployment block generated by the source system. The content deployment block includes top level content of the deployment set, dependent content in which the top level content depends from, and discharge instructions for the deployment set. The discharge instructions include dependency ordered deployment commands, and the top level content includes content that is specified by a user for deployment. The system also includes a target system configured to receive the content deployment block from the source system.

DETAILED DESCRIPTION OF THE INVENTION

The methods and systems described herein facilitate managing clinical content dependency deployment in content management systems by using content deployment blocks (CDB). Although content deployment in a content management system (CMS) is described herein in detail, it should be appreciated that the exemplary methods and systems are applicable to clinical information systems (CIS) describe herein. It should also be appreciated that application of the exemplary methods and systems would be understood by persons of ordinary skill in the art. Therefore, a detailed description of CIS utilizing the exemplary methods and systems is not provided.

The methods and systems described herein are believed to be applicable to many different industries for retrieving many different types of data. The exemplary embodiment described herein is the healthcare industry. Although the healthcare industry is the exemplary industry described herein, the invention is in no way limited to the healthcare industry.

Exemplary embodiments of systems and processes that facilitate integrated network-based electronic data entry and workflow process management related to a Content Management System (CMS) for the healthcare industry are described below in detail. The systems and processes facilitate, for example, electronic submission of information using a client system and email alerts for system users. A technical effect of the systems and processes described herein include at least one of permitting a healthcare provider to obtain and share clinical data. More specifically, in the exemplary embodiment, a healthcare provider such as, but not limited to, a clinician, a physician and/or a nurse utilizes the CMS to manage, track, retain, and edit physician order entry and/or processing, physician and/or nursing documentation, physician and/or nursing dose charting and/or medication administration record (MAR), registration, and/or scheduling related to patients. The information may then be shared internally and/or across a network with other authorized individuals or organizations.

Figure 1:
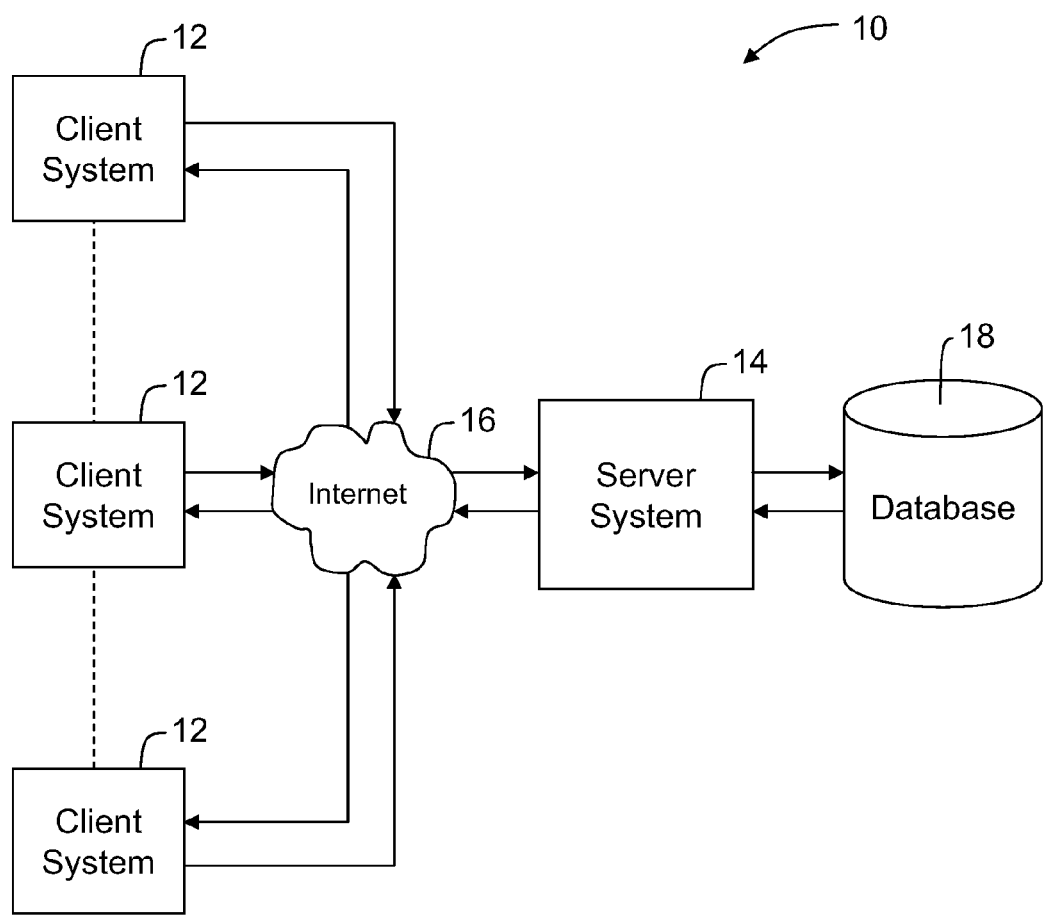
FIG. 1 is a simplified block diagram of an exemplary Content Management System (CMS)

FIG. 1 is a simplified block diagram of an exemplary Content Management System (CMS) 10 including a plurality of client sub-systems, also referred to as client systems 12, and a server system 14. Client systems 12 include any device capable of interconnecting to the Internet 16 including a web-based phone, a personal digital assistant (PDA), or other web-based connectable devices. In one embodiment, client systems 12 are PDAs including a web browser, such that server system 14 is accessible to client systems 12 using Internet 16. Client systems 12 are interconnected to Internet 16 through many interfaces including a network, such as a local area network (LAN) or a wide area network (WAN), dial-in-connections, cable modems and special high-speed ISDN lines.

Server system 14 is connected to a centralized database 18 that contains clinically related information. In one embodiment, database 18 is stored on server system 14 and can be accessed by users at one of client systems 12 by logging onto server system 14 through one of client systems 12. In an alternative embodiment, database 18 is stored remotely from server system 14 and may be non-centralized.

Figure 2:
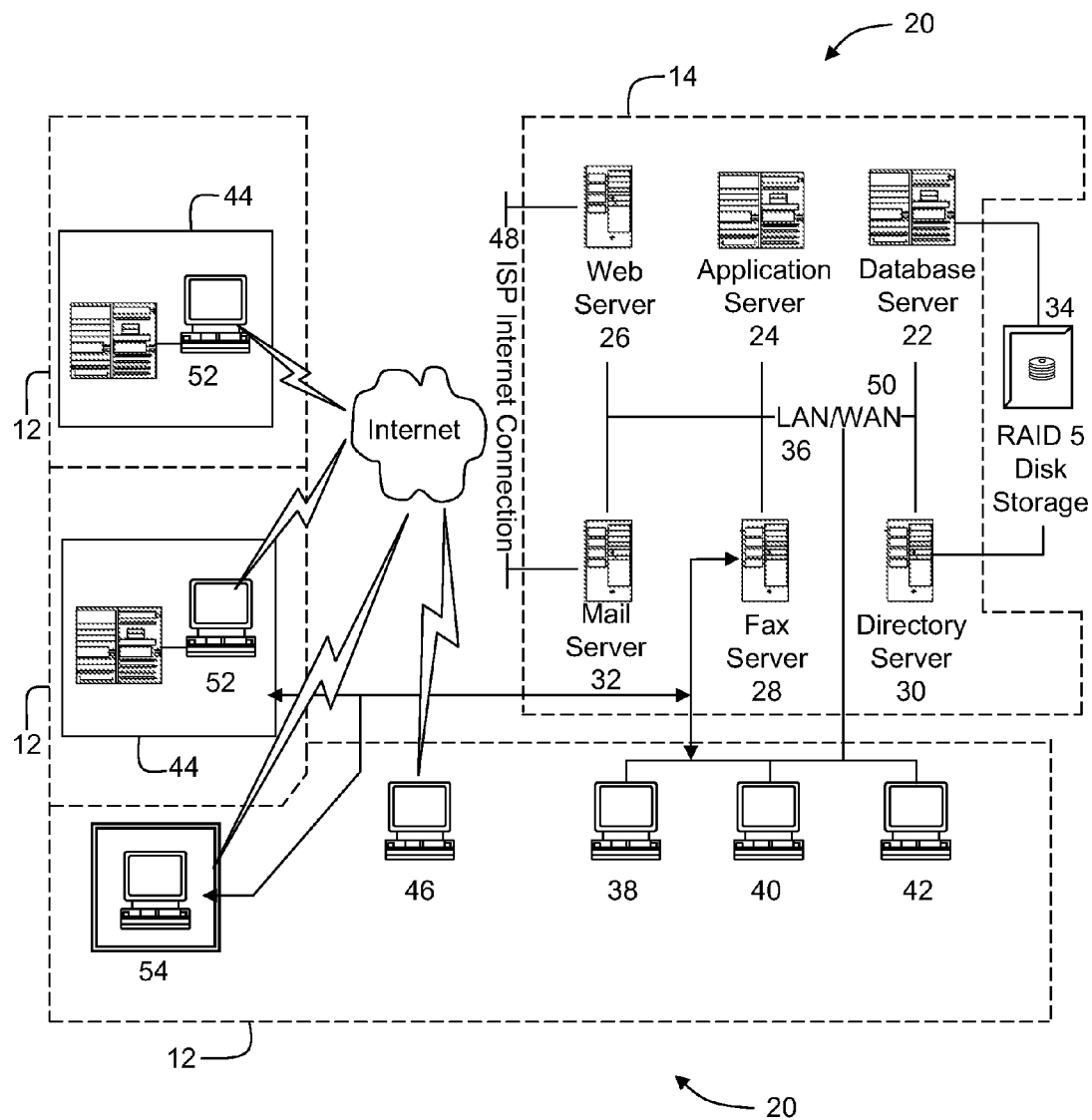
FIG. 2 is an expanded block diagram of a server architecture of the CMS.

FIG. 2 is an expanded block diagram of an exemplary embodiment of a server architecture of CMS 20. Components in CMS 20, identical to components of CMS 10 (shown in FIG. 1), are identified in FIG. 2 using the same reference numerals as used in FIG. 1. CMS 20 includes server system 14 and client systems 12. In one embodiment, server system 14 includes a plurality of conventional servers such as, but not limited to, a database server 22, an application server 24, a web server 26, a fax server 28, a directory server 30, and a mail server 32.

Database server 22 is any database application that manages the processing of data queries by following client/server architecture models to facilitate computer related tasks such as, but not limited to, collecting, displaying, analyzing, storing, retrieving, and/or manipulating data. Application server 24 is a middle-tier software and hardware combination that runs one or more applications to perform a few specific application tasks such as, but not limited to, interpreting site traffic, constructing pages, and/or delivering content to the Web based on a dynamic content repository. Web server 26 is a server that manages, retrieved and/or transfers web based applications over the Internet as they are requested using one or more protocols such as, but not limited to, HTTP and/or FTP. Fax server 28 is a specialized network server that can send, receive, and/or redirect faxes, alphanumeric pages, and/or email messages on a telemessaging platform. Directory server 30 is a server that manages large directories of digital data and provides access to the data that is contained in the directories. Mail server 32 is an application that controls the distribution and storage of email messages. In one embodiment, a disk storage unit 34 is coupled to directory server 30 and database server 22.

Servers 22, 24, 26, 28, 30, and 32 are coupled to a local area network (LAN) 36. In addition, a system administrator's workstation 38, a user workstation 40, and a supervisor's workstation 42 are also coupled to LAN 36. Alternatively, workstations 38, 40, and 42 are coupled to LAN 36 using an Internet link or are connected through an Intranet. Each workstation 38, 40, and 42 is a personal computer having a web browser. Although the functions performed at the workstations typically are illustrated as being performed at respective workstations 38, 40, and 42, such functions can be performed at one of many personal computers coupled to LAN 36. Workstations 38, 40, and 42 are illustrated as being associated with separate functions only to facilitate an understanding of the different types of functions that can be performed by individuals having access to LAN 36.

Server system 14 is configured to be communicatively coupled to various authorized user client systems such as, but not limited to, client systems 44 of physicians and/or client system 46 of nurses that each uses an Internet Service Provider (ISP) Internet connection 48. The communication in the exemplary embodiment is illustrated as being performed using the Internet, however, any other wide area network (WAN) 50 type communication can be utilized in other embodiments, i.e., the systems and processes are not limited to being practiced using the Internet. In the exemplary embodiment, any authorized user having a workstation 52 can access CMS 20. At least one of the client systems 12 includes a manager workstation 54 located at a remote location. Workstations 52 and 54 are personal computers having a web browser and configured to communicate with server system 14.

Figure 3:
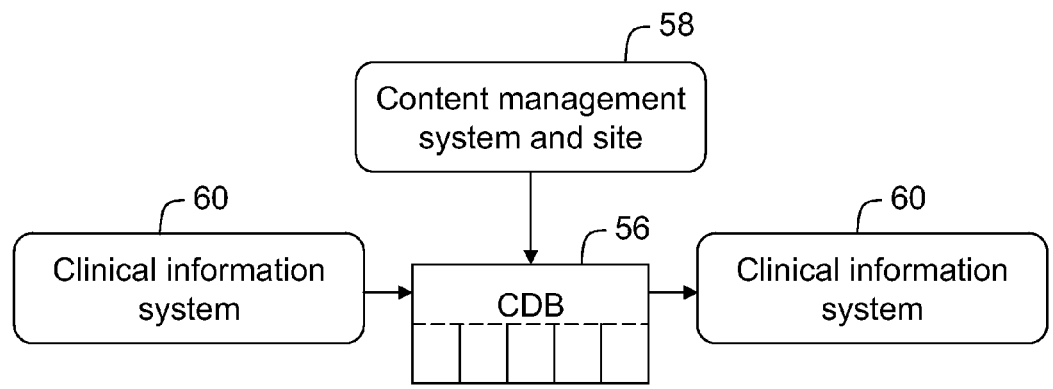
FIG. 3 is a block diagram of content transfer between multiple systems using an exemplary content deployment block (CDB)

FIG. 3 is a block diagram of content transfer between multiple systems using an exemplary content deployment block (CDB) 56. In one embodiment, CDB 56 is transferred from a content management system and site (CMSS) 58 to a clinical information system (CIS) 60. Alternatively, CDB 56 is transferred from one CIS 60 to another CIS 60. In one embodiment, a single CDB 56 is generated from either content management systems or clinical information systems. However, it should be appreciated that each CDB is generated by a single system and each content management system or clinical information system may generate a plurality of CDBs. Further, it should be appreciated that each CDBs may be generated by any single transmitting source system and transferred to any receiving target system in which the source and target systems are capable of resolving terminology and knowledge content dependencies as described in detail below.

Figure 4:
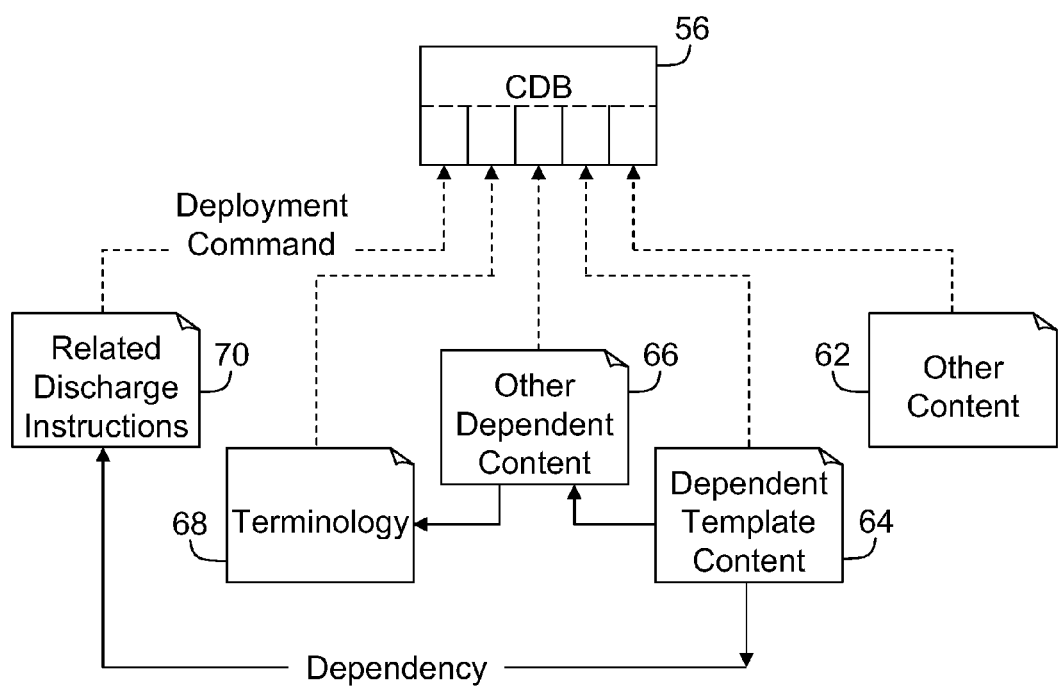
FIG. 4 is a block diagram of the exemplary CDB shown in FIG. 3.

FIG. 4 is a block diagram of exemplary content deployment block (CDB) 56. As discussed above, each CDB 56 may be generated by any transmitting source system capable of resolving terminology and knowledge content dependencies as described in detail below. In the exemplary embodiments described below, CDB 56 is described as being generated by a content management system, such as content management system and site (CMSS) 58. It should be appreciated that generation of CDB 56 by other transmitting source systems that are capable of resolving terminology and knowledge content dependencies would be understood by persons of ordinary skill in the art. Therefore, a detailed description of generating CDB 56 by clinical information systems (CIS) 60 is not provided.

In one embodiment, CDB 56 includes any clinical content specified to be transferred and all content that the specified clinical content depends on. Dependency relationships are created between clinical content and other content and/or system resources, for example, when the clinical content is authored, changed, and/or captured. Top level (root/parent) clinical content can then be associated with one or more deployment sets. Each deployment set is associated with a particular deployment and/or a specific set of content which could then be sold and/or deployed at run-time.

In one embodiment, CMSS 58 takes each top level clinical content piece from a deployment set and determines all dependencies for the respective top level content. For example, a deployment set may include various types of top level content, which is content that is specified by a user for deployment. If other content 62 is specified, the system determines that no additional content is used to form other content 62. If dependent template content 64 is specified, the system determines that additional content such as dependent template content 64, other dependent content 66, and terminology 68 are used to form dependent template content 64. The dependencies of dependent template content 64 are identified by pointers to other dependent content 66 and terminology 68.

CMSS 58 determines and resolves the dependency for dependent template content 64 to include in related discharge instructions 70, which form part of CDB 56. Related discharge instructions 70 are an encoded stream of commands incorporated into a deployment command. The command order facilitates assuring that dependent template content 64 is not deployed until its dependencies are deployed. CMSS 58 places other content 62, dependent template content 64, other dependent content 66, terminology 68, and specified related discharge instructions 70, which includes the dependency, in CDB 56.

In other words, all the dependencies for the clinical knowledge of dependent template content 64 are gathered in appropriate form and specified in CDB 56. As such, any specified top level content and all content that the top level content depends on is applied or deployed to a target system in a predetermined order, at a predetermined time, and/or for a particular time frame. As a result, a deployment set's direct dependencies on system resources and applications can be streamed as a smaller set of commands that can be used by a target system to determine if a particular CDB can be deployed at that target site such that the content functions in the same way as in the source system.

In one embodiment, the source and target systems include content that is consistent and common between all applications. For example, if common terminology is already deployed on the target system, there is no need to redeploy the same terminology. Therefore, deployment of CDB 56 may be implemented to make changes in the target system reversible by using conventional patterns such as, but not limited to, history, command, and/or memento patterns. For example, the target system can uninstall CDB 56 by reversing the command line. As such, the target system receiving CDB 56 has a way of filtering, detecting and/or comparing some content and making changes to the target system reversible using reversible command patterns.

Figure 5:
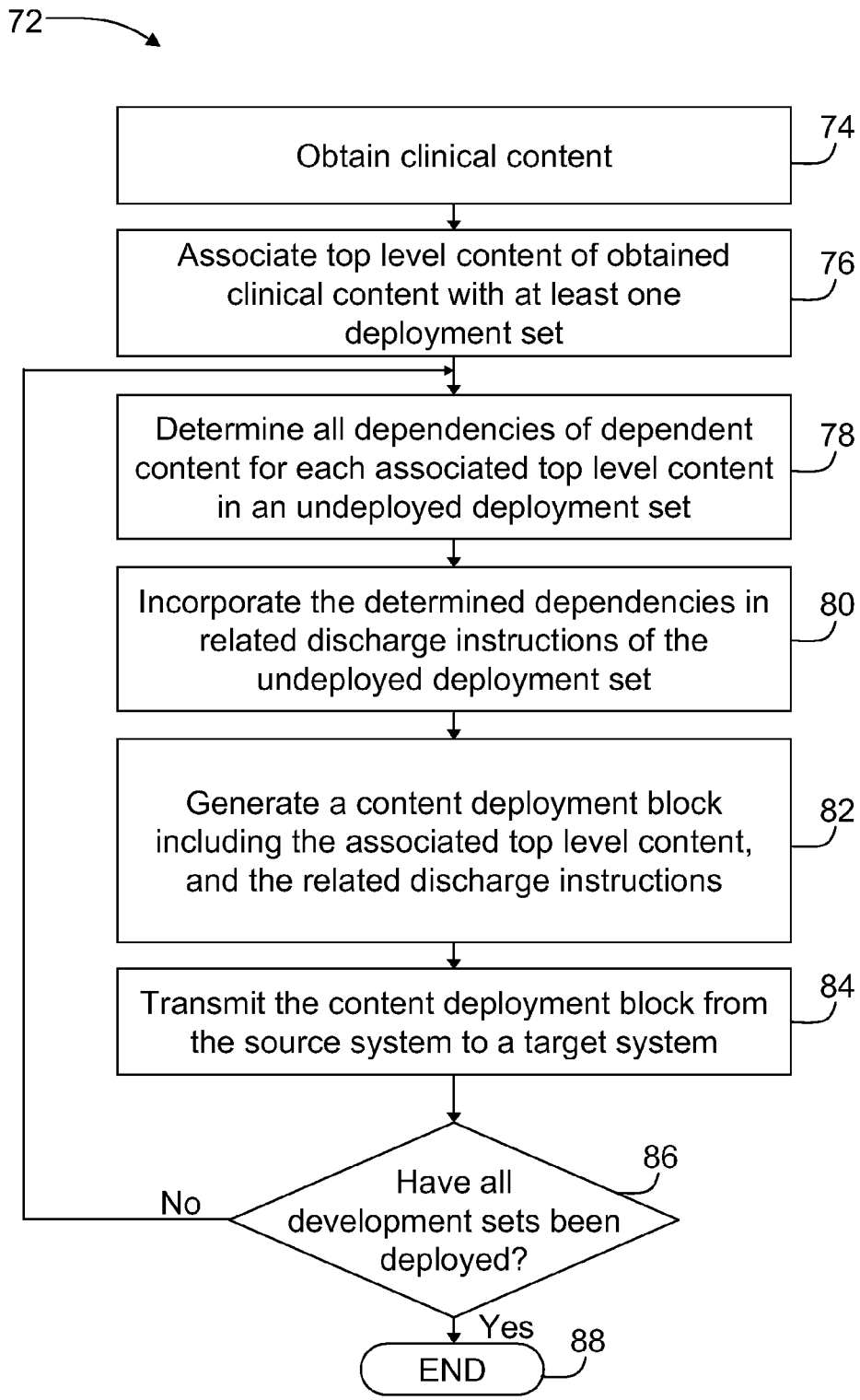
FIG. 5 is a flowchart illustrating exemplary processes for generating the exemplary CDB shown in FIGS. 3 and 4.

FIG. 5 is a flowchart 72 illustrating exemplary processes for generating exemplary CDB 56 (shown in FIGS. 3 and 4). In the exemplary embodiments described below, CDB 56 is described as being generated by a source content management system, such as content management system and site (CMSS) 58. It should be appreciated that generation of CDB 56 by other transmitting source systems that are capable of resolving terminology and knowledge content dependencies would be understood by persons of ordinary skill in the art. Therefore, a detailed description of generating CDB 56 by clinical information systems (CIS) 60 is not provided.

In one embodiment, CMSS 58 obtains 74 clinical content associated with patients. In the exemplary embodiment, clinical content includes data and/or documents that are received and entered into CMSS 58 either manually or electronically. Once clinical content has been digitally stored in CMSS 58, the information is easily accessible through any computer system or similar device.

In one embodiment, clinical content is collected from any connected data input source such as, but not limited to, a facsimile machine, a scanner, a patient monitor, and/or a multifunctional device. Clinical content is also collected from an application of an authorized healthcare individual such as, but not limited to, physicians, nurses, pharmacists and/or clerks charting patient admission, medication, lab results, and/or any other patient related data. As described previously, clinical content includes any information associated with patients such as, but not limited to, lab results, medication orders, vital signs information, physician or nurse documentation, and/or any information that is part of a patient record. Clinical content may also include any electronic templates and/or forms used to obtain the information associated with a patient.

Each top level content (root/parent) of the obtained clinical content is associated 76 with at least one deployment set. In one embodiment, the top level content includes other content 62 and dependent template content 64 (shown in FIG. 4). Then, all dependencies of dependent content for each associated top level content in an undeployed deployment set is determined 78. In one embodiment, the dependent content for dependent template content 64 includes other dependent content 66 and terminology 68 (shown in FIG. 4). However, there are no dependent content for other content 62.

The determined dependencies are then incorporated 80 into related discharge instructions. In one embodiment, the dependency relationship of dependent template content 64, other dependent content 66, and terminology 68 is incorporated into related discharge instructions 70 for the deployment set (shown in FIG. 4). Related discharge instructions 70 issue a deployment command for the deployment set.

A content deployment block is generated 82 for the deployment set. In one embodiment, CDB 56 includes other content 62, dependent template content 64, other dependent content 66, terminology 68, and related discharge instructions 70 that issue the deployment command. Next, the content deployment block is transmitted 84 from the source system to a target system. In one embodiment, CDB 56 is transmitted from CMSS 58 to clinical information system (CIS) 60 (shown in FIG. 3) so the associated content can be used by CIS 60.

The source system such as CMSS 58 then determines 86 if all deployment sets have been deployed. If all deployment sets have not been deployed, operation jumps back and again determines 78 all dependencies of dependent content for each associated top level content in any undeployed deployment sets. If all deployments sets have been deployed, operation ends 88.

It should be appreciated that although the example discussed above is related to the heath care industry, the content management systems (CMS) and/or clinical information systems (CIS) that generate content deployment blocks may be used in any other business or field of endeavor involving records and documentation. For example, CMS and/or CIS can also be used in the financial industry including the phases of tracking market patterns for a product and/or service. Further, it should be appreciated that the systems and processes are not limited to the specific embodiments described herein. In addition, components of each system and each process can be practiced independently and separately from other components and processes described herein. Each component and process also can be used in combination with other assembly packages and processes.

In the exemplary embodiments described above, exemplary content management systems and clinical information systems generate a stream of dependency ordered deployment commands. It should be appreciated that the stream of dependency ordered deployment commands can be Extensible Markup Language (XML), HyperText Markup Language (HTML), and/or any other knowledge format. It should also be appreciated that content deployment blocks (CDBs) are independent of the protocol used to transfer information between source and target systems. As such, the CDBs can be transferred using any protocol such as, but not limited to, a Hypertext Transfer Protocol (HTTP) and a File Transfer Protocol (FTP).

In the exemplary embodiments, content management systems and/or clinical information systems are configured resolve dependencies to generate dependency ordered deployment commands that are packaged within content deployments blocks along with terminology and knowledge content. As a result, such exemplary clinical content dependency deployment management systems and methods facilitate sharing clinical knowledge and facilitate deploying a CDB received at a target system/site. For example, users of a target system can call up/pull out one piece of content in a content deployment block that contains both terminology and knowledge with dependencies installed in the right place, in the right order, and at the right time.

In the exemplary embodiments, the content deployment blocks include dependency ordered deployment commands to facilitate reducing run-time deployment problems. For example, the content deployment blocks facilitate increasing access to clinical content by reducing problems of interoperation so that a target system experiences less broken links, broken images, and/or lengthy run-time deployment. As such, the content deployments blocks facilitate deploying content across various customers and heterogeneous environments without intervention and/or technical assistance. Additionally, the content deployments blocks facilitate the following: automatically distributing and sharing content from a centralized content repository to all customers; internet selling and downloading of rules, protocols, care plans, and terminology with respect to a certain applications; and deploying sessions of content to development, testing, and production environments. As a result, content integration is facilitated for on-demand clinical decision support based on expert knowledge delivered to the right person, through the right channel, and at the right time.

Exemplary embodiments of methods and systems for managing clinical data are described in detail above. The methods and systems are not limited to the specific embodiments described herein or to the specific illustrated clinical content dependency deployment management methods and systems.

While the invention has been described in terms of various specific embodiments, those skilled in the art will recognize that the invention can be practiced with modification within the spirit and scope of the claims.

What is claimed is:

1. A method for managing electronic content in a Content Management System (CMS) including a plurality of client sub-systems communicatively coupled to a server system through a network, said method comprising:
    obtaining by the CMS clinical content associated with patients;
    associating top level contents of the obtained content with a deployment set, wherein the deployment set includes the top level content that is specified by a user for deployment;
    determining all dependencies of dependent content for each of the associated top level contents in the deployment set;
    incorporating the determined dependencies into discharge instructions for the deployment set;
    generating a content deployment block including the associated top level contents, the dependent content, and the discharge instructions for the deployment set, the discharge instructions including dependency ordered deployment commands, and
    transferring the content deployment block to a target client system so that the specified top level content and all content that the top level content depends on is deployed to the target client system in a predetermined order, at a predetermined time, and for a particular time frame.

2. A method in accordance with claim 1 wherein obtaining the content comprises obtaining at least one of terminology content and knowledge content.

3. A method in accordance with claim 1 wherein generating a content deployment block further comprises providing dependency ordered eXtensible Markup Language (XML) commands.

4. A method in accordance with claim 1 wherein obtaining the content comprises obtaining clinical content.

5. A method in accordance with claim 1 wherein obtaining the content comprises obtaining content by a source system.

6. A method in accordance with claim 5 further comprising transmitting the content deployment block from the source system to a target system.

7. A method in accordance with claim 6 further comprising redeploying the content deployment block from the target system to the source system.

8. A method in accordance with claim 5 wherein obtaining content by a source system comprises obtaining content by at least one of a content management system and a clinical information system.

9. A system including a plurality of client sub-systems communicatively coupled to a server system through a network for managing electronic content, said system comprising:
    a source client sub-system capable of resolving terminology and knowledge content dependencies and configured to:
    obtain said content;
    associate top level contents of said obtained content with a deployment set associated with at least one of a particular deployment and a specific set of content;
    determine all dependencies of dependent content for each of said associated top level contents in said deployment set; and
    incorporate said determined dependencies into discharge instructions for said deployment set, said top level content includes content that is specified by a user for deployment; and
    a content deployment block generated by said source client sub-system, said content deployment block including said associated top level contents, said dependent content, and said discharge instructions for said deployment set, said discharge instructions including dependency ordered deployment commands, where
    the source client sub-system is further configured to transfer the content deployment block to a target client system so that the specified top level content and all content that the top level content depends on is deployed to the target client system in a predetermined order, at a predetermined time and for a particular time frame.

10. A system in accordance with claim 9 wherein said content comprises at least one of terminology content and knowledge content.

11. A system in accordance with claim 9 wherein said dependency ordered deployment commands are eXtensible Markup Language (XML) commands.

12. A system in accordance with claim 9 wherein said content comprises clinical content.

13. A system in accordance with claim 9 further comprising a target system configured to receive said content deployment block.

14. A system in accordance with claim 13 wherein said target system is configured to redeploy said content deployment block from said target system to said source client sub-system.

15. A system in accordance with claim 9 wherein said source client sub-system comprises at least one of a content management system and a clinical information system.

16. A system including a plurality of client sub-systems communicatively coupled to a server system through a network for managing electronic content of a deployment set, said system comprising:
- a source client sub-system capable of resolving terminology and knowledge content dependencies; and
- a content deployment block generated by said source client sub-system, said content deployment block including top level content of the deployment set, dependent content in which said top level content depends from, and discharge instructions for the deployment set, said discharge instructions including dependency ordered deployment commands, said top level content including content that is specified by a user for deployment; and
- a target client system capable of resolving terminology and knowledge content dependencies and configured to receive said content deployment block from said source client sub-system, where
- the source client sub-system is further configured to transfer the content deployment block to a target client system so that the specified top level content and all content that the top level content depends on is deployed to the target client system in a predetermined order, at a predetermined time and for a particular time frame.

17. A system in accordance with claim 16 wherein said content comprises at least one of terminology content and knowledge content.

18. A system in accordance with claim 16 wherein said dependency ordered deployment commands are eXtensible Markup Language (XML) commands.

19. A system in accordance with claim 16 wherein said content comprises clinical content.

20. A system in accordance with claim 16 wherein said target client system is configured to redeploy said content deployment block from said target client system to said source client sub-system.

* * * * *